United States Patent
Fukuoka et al.

[11] Patent Number: 6,086,453
[45] Date of Patent: Jul. 11, 2000

[54] WAFER PATTERN IMAGING APPARATUS

[75] Inventors: Kazuya Fukuoka; Kazuhiro Yagi; Fusao Hoshino, all of Mitaka, Japan

[73] Assignee: Tokyo Seimitsu Co., Ltd., Tokyo, Japan

[21] Appl. No.: 09/310,759

[22] Filed: May 13, 1999

[30] Foreign Application Priority Data

May 20, 1998 [JP] Japan .................................. 10-138625

[51] Int. Cl.⁷ .............................. B24B 49/00; B24B 51/00
[52] U.S. Cl. ...................................... 451/5; 451/6
[58] Field of Search .................................. 451/5, 6, 28, 1, 451/8, 9, 10, 54, 53, 41; 125/13.01; 83/62; 250/491.1, 206.1, 221, 222; 438/463; 156/295

[56] References Cited

U.S. PATENT DOCUMENTS

| | | | |
|---|---|---|---|
| 4,407,262 | 10/1983 | Wirz et al. | 451/6 |
| 5,353,551 | 10/1994 | Nishida | 451/6 |
| 5,417,791 | 5/1995 | Beeteson et al. | 156/295 |
| 5,433,649 | 7/1995 | Nishida | 451/6 |
| 5,668,061 | 9/1997 | Herko et al. | 438/463 |

FOREIGN PATENT DOCUMENTS

| | | |
|---|---|---|
| 6-232255 | 8/1994 | Japan . |
| 7-75955 | 3/1995 | Japan . |
| 8-264488 | 10/1996 | Japan . |

*Primary Examiner*—Derris H. Banks
*Attorney, Agent, or Firm*—Oliff & Berridge, PLC

[57] ABSTRACT

Even if it is impossible to image a pattern surface of a wafer that is placed with its down on a wafer table with visible light, a wafer pattern imaging apparatus is able to image the pattern surface (the obverse) from the reverse of the wafer with light transmitted through the wafer. The obverse of the wafer, made of silicon, is attached to a wafer sheet to protect the obverse of the wafer, on which patterns are formed. An infrared camera, which images an image formed by infrared light, and an infrared light source, which emits the infrared light to the wafer, are disposed above the wafer table. A mirror for reflecting the infrared light is disposed in the wafer table. The infrared light emitted from the infrared light source is transmitted through the wafer. Then, the infrared light is reflected on the mirror, and the reflected infrared light illuminates the pattern surface of the wafer. The infrared camera images the images of the pattern surface.

10 Claims, 8 Drawing Sheets

F I G. 7
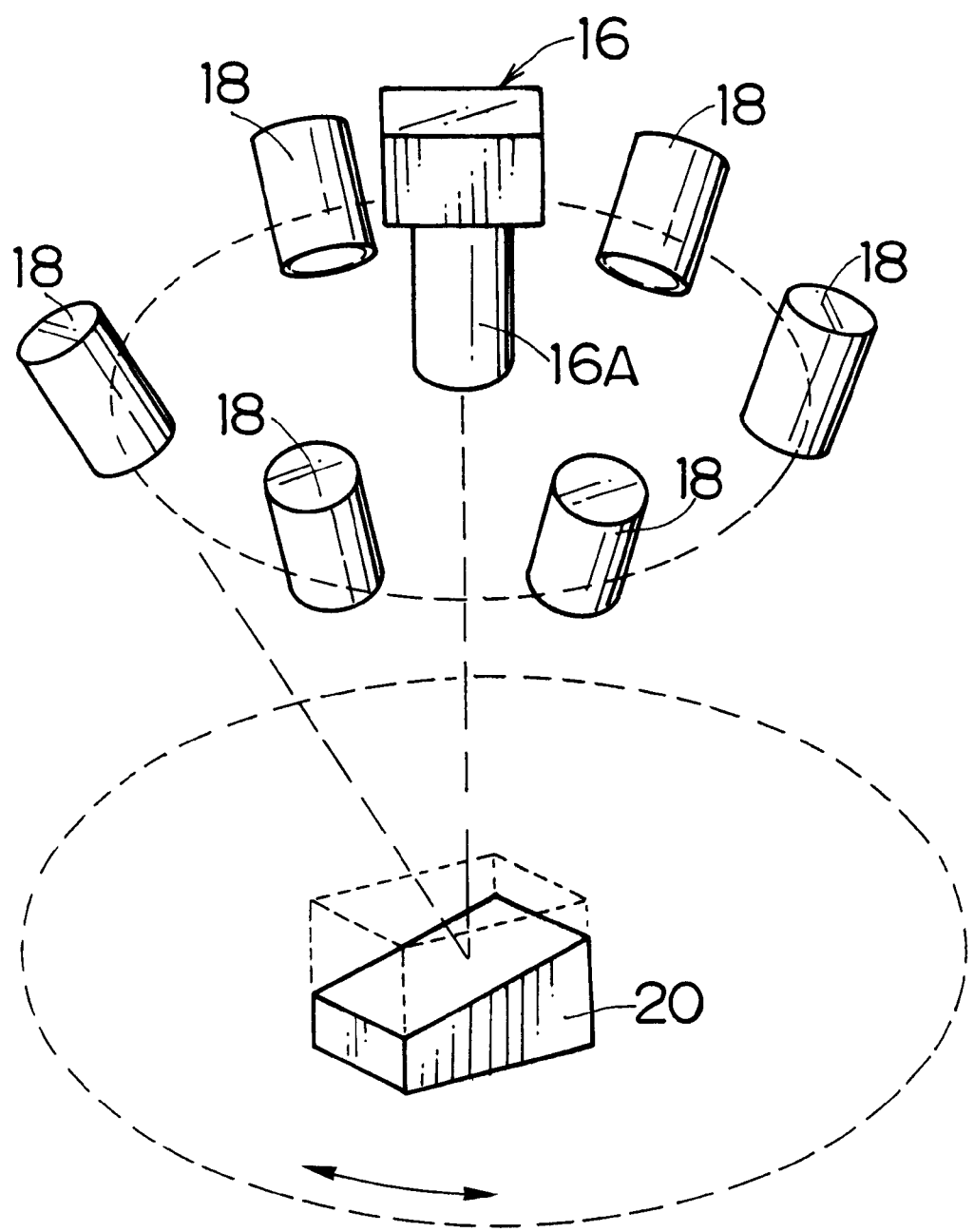

F I G. 9
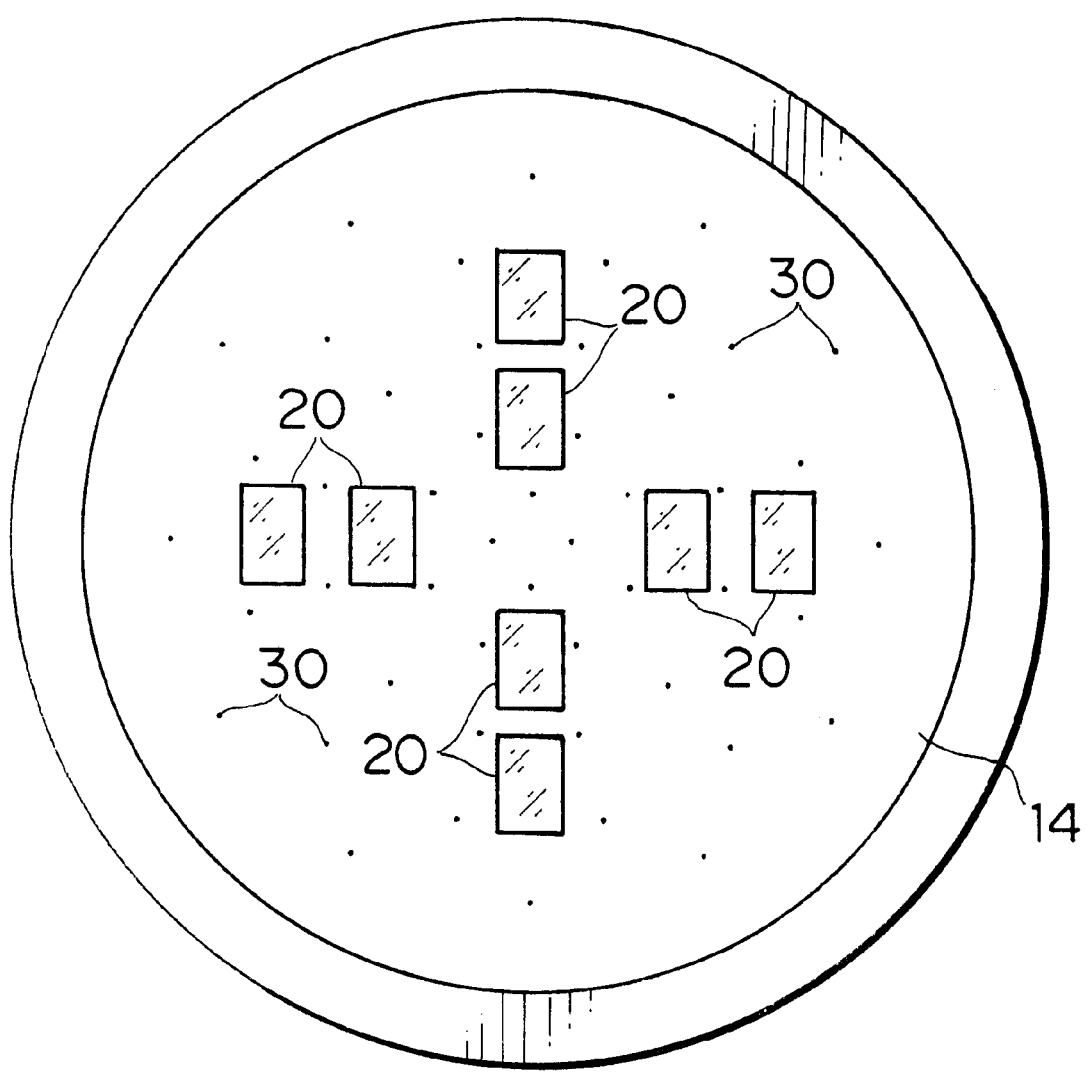

WAFER PATTERN IMAGING APPARATUS

BACKGROUND OF THE INVENTION

1. Field of the Invention

The present invention relates generally to a wafer pattern imaging apparatus, and more particularly to a wafer pattern imaging apparatus that is applied to align a wafer in a wafer dicing apparatus, or the like.

2. Description of Related Art

Conventionally, a wafer is diced into a number of chips as described below. First, a wafer mounter aligns the wafer with a frame for transporting the wafer, and adheres the wafer to an adhesive tape (which will hereafter be referred to as a wafer sheet) that is adhered to the frame. The wafer as well as the frame is transferred to a wafer table, on which the wafer is diced. The reverse of the wafer, on which no pattern is formed, is adhered to the wafer sheet, and the wafer is placed with its obverse (which will hereafter be referred to as a pattern surface) up on the wafer table.

Then, the wafer is aligned on the wafer table. A pattern matching method is already known for aligning the wafer. In the pattern matching method, the pattern surface of the wafer is imaged at a plurality of positions thereof, and the obtained images are compared with a reference pattern stored in a computer to find a position of the reference pattern on the wafer. The position of the wafer is determined from the position of the reference pattern. The position of the wafer table is adjusted in accordance with the determined position of the wafer so as to properly align the wafer.

The wafer, which is adhered to the wafer sheet, is diced into a number of chips with a blade such as a diamond cutter. After the dicing, swarf cut from the wafer in the dicing is washed away by pure water, etc. Then, the chips are detached from the wafer sheet, and the dicing is completed.

In the dicing process, however, contaminations such as the swarf are adhered to the pattern surface of the wafer. Conventionally, the contaminations are washed away by pure water, etc. after the wafer is diced as stated above, or a cutting solution is supplied to the wafer during the dicing in such a manner as to prevent the contaminations from being adhered to the wafer. In these methods, it is impossible to eliminate the contaminantions from the pattern surface of the wafer.

Moreover, the cutting solution, etc. must not contact with the pattern surfaces of some kinds of wafers. In this case, it requires a great deal of trouble to prevent the contaminations from being adhered to the wafer. For example, the pattern surface of the wafer must be covered with a protection film, or the like.

To eliminate the above-mentioned disadvantages, the pattern surface of the wafer may be adhered to the wafer sheet to protect the pattern surface. This prevents the cutting solution, etc. from contacting with the pattern surface of the wafer and prevents the contaminations from being adhered to the pattern surface of the wafer.

In this case, however, the wafer is placed with its pattern surface down on the wafer table, and thus, an ordinary camera cannot image the pattern surface of the wafer from above the wafer table. Therefore, it is impossible to align the wafer according to the images of the pattern surface in the pattern matching method.

SUMMARY OF THE INVENTION

In view of the foregoing, it is an object of the present invention to provide a wafer pattern imaging apparatus which is able to image the pattern surface of the wafer from the reverse thereof with light which is transmitted through the wafer, even if the pattern surface of the wafer cannot be imaged with visible light because the wafer is placed with its pattern surface down on the wafer table.

To achieve the above-mentioned object, the present invention is directed to a wafer pattern imaging apparatus for imaging patterns on an obverse of a wafer, the wafer pattern imaging apparatus comprising: an illumination means for emitting light to the wafer, the light being capable of being transmitted through the wafer except for parts of the patterns; and an imaging means for imaging the patterns on the obverse of the wafer by the light emitted from the illumination means and transmitted through the wafer.

If the wafer is made of silicon, the light is infrared light, and the imaging means comprises an infrared camera.

The wafer pattern imaging apparatus is preferably characterized in that: the wafer is placed with the obverse thereof down on a wafer table; the imaging means and the illumination means are disposed above a reverse of the wafer; the wafer table has a reflection member built-in for reflecting the light emitted from the illumination means and transmitted through the wafer to the imaging means; and the imaging means images an image formed by the light reflected by the reflection member.

The wafer pattern imaging apparatus is preferably characterized in that: the wafer is placed with the obverse thereof down on a wafer table; the imaging means is disposed above a reverse of the wafer; the illumination means is built in the wafer table; and the imaging means images an image formed by the light emitted from the illumination means.

According to the present invention, the light such as the infrared light, which can be transmitted through the wafer made of silicon, is emitted to illuminate the wafer, and the patterns on the obverse of the wafer is imaged with the light transmitted through the wafer. The patterns on the obverse of the wafer can be imaged from the reverse of the wafer. It is therefore possible to image the patterns on the obverse of the wafer from above the wafer table, even if the obverse of the wafer is attached to the wafer sheet and the wafer is placed with its obverse down on the wafer table in the wafer dicing machine in order to prevent the contaminations from being adhered to the obverse of the wafer, on which the patterns are, or prevent the cutting solution from contacting with the obverse of the wafer. The wafer can be aligned in accordance with the obtained images.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 7 is a view showing another IR light source;

FIG. 9 is a plan view showing another preferred embodiment of the arrangement of mirrors on the wafer table;

DETAILED DESCRIPTION OF THE PREFERRED EMBODIMENT

This invention will be described in further detail by way of example with reference to the accompanying drawings.

Figure 1:
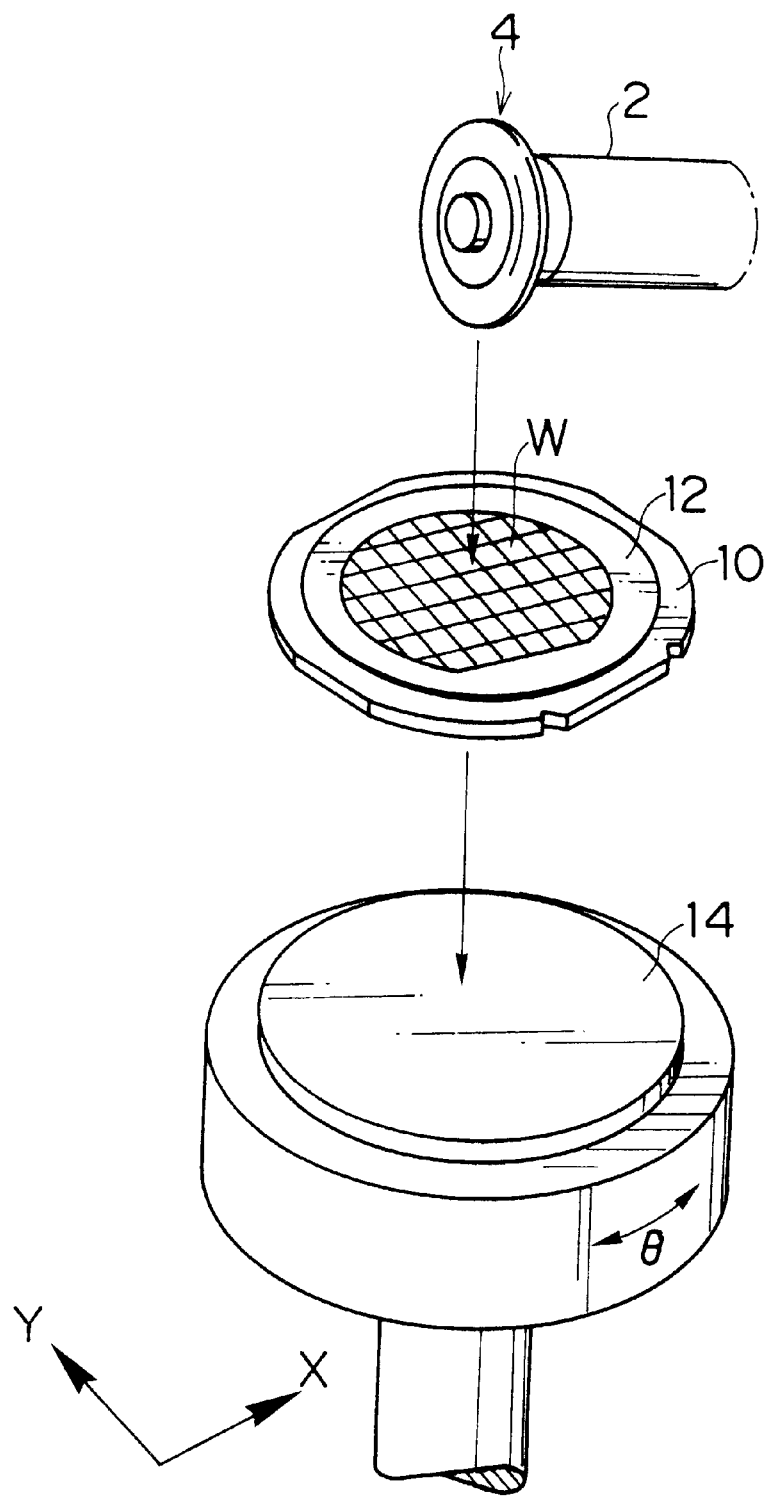
FIG. 1 is a view showing a preferred embodiment of a wafer dicing apparatus to which the present invention is applied.
Figure 2:
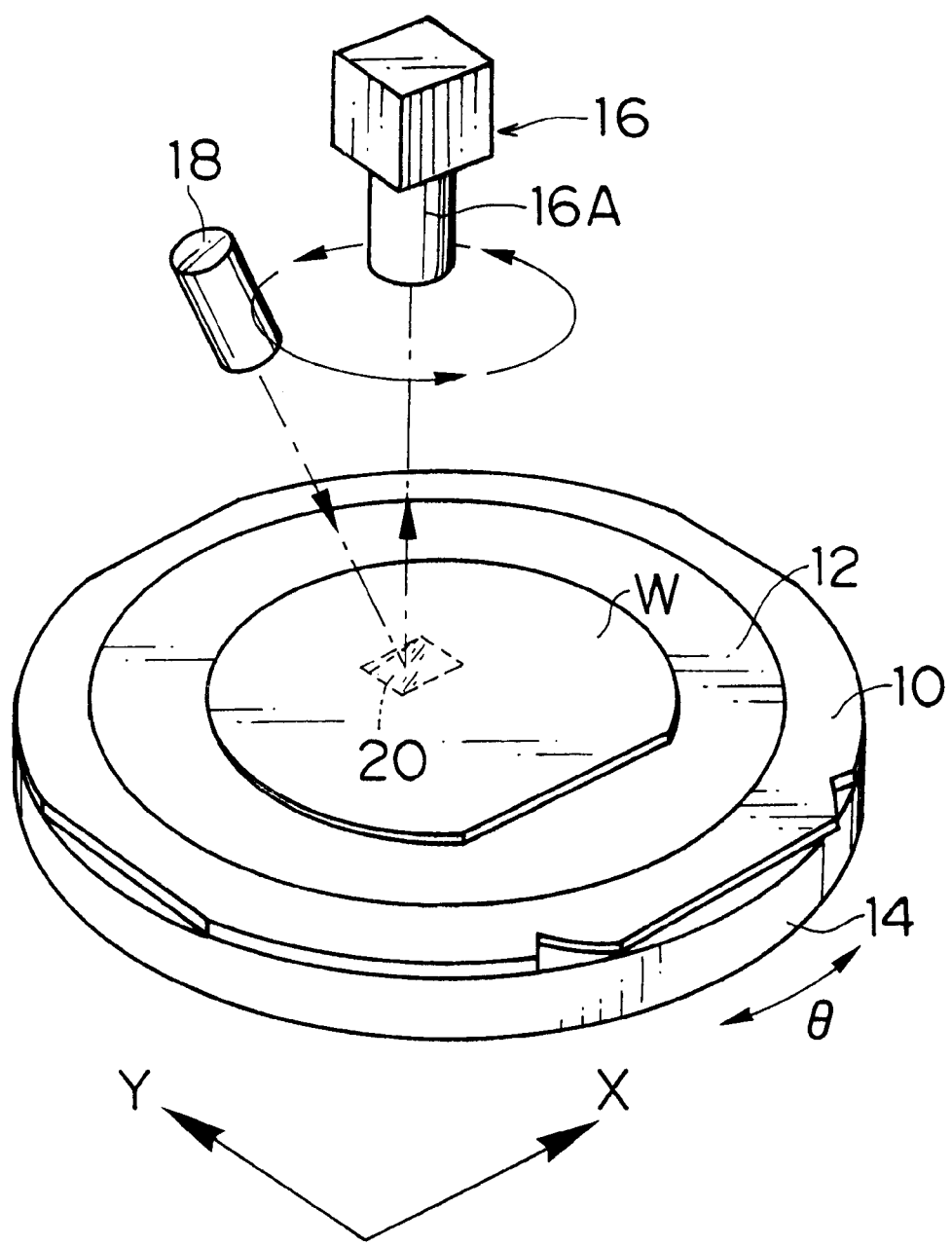
FIG. 2 is a view showing a preferred embodiment of a wafer pattern imaging apparatus according to the present invention.

FIGS. 1 and 2 show a wafer dicing apparatus and a wafer pattern imaging apparatus according to an embodiment of the present invention, which is applied to align a wafer in the wafer dicing apparatus. A wafer (e.g., a silicon wafer) W is attached to a wafer sheet 12, which is attached to a frame 10, and is placed on a wafer table 14 with the frame 10. The obverse of the wafer W, on which patterns are formed (which will hereafter be referred to as a pattern surface), is attached to the wafer sheet 12, and the wafer W attached to the wafer sheet 12 is placed with its pattern surface down on the wafer table 14.

The wafer table 14 holds the lower surface of the wafer sheet 12 by suction, and fixes the wafer W thereon. The wafer table 14 is capable of moving along the X and Y axes and rotating in a direction θ in FIGS. 1 and 2. A control part (not shown) controls the wafer table 14 so that the wafer W held on the wafer table 14 can be moved to a desired position.

As shown in FIG. 1, the wafer dicing apparatus has a blade 4, which is rotated at a high speed by a drive motor 2. The rotating blade 4 dices the wafer W on the wafer table 14 into chips. The wafer dicing apparatus supplies a cutting solution and cleaning water through a cutting solution jetting nozzle (not shown) and a cleaning water jetting nozzle (not shown). The cutting solution and the cleaning water cool and clean the blade 4 and the wafer W. Since the pattern surface of the wafer W is attached to the wafer sheet 12, the wafer sheet 12 protects the pattern surface of the wafer W to thereby prevent the cutting solution from contacting the pattern surface and prevent contaminations from being adhered to the pattern surface during the dicing.

The pattern imaging apparatus in FIG. 2 is used to align the wafer W in the wafer dicing apparatus. As shown in FIG. 2, an infrared (IR) camera 16 is disposed above the wafer table 14 in order to image images formed by infrared light and to visualize the images. An IR light source 18 is also disposed above the wafer table 14 in order to illuminate the wafer W on the wafer table 14 with the infrared light, and the IR light source 18 is capable of rotating around the IR camera 16. The IR camera 16 has a microscope 16A, which enlarges the images.

Figure 3:
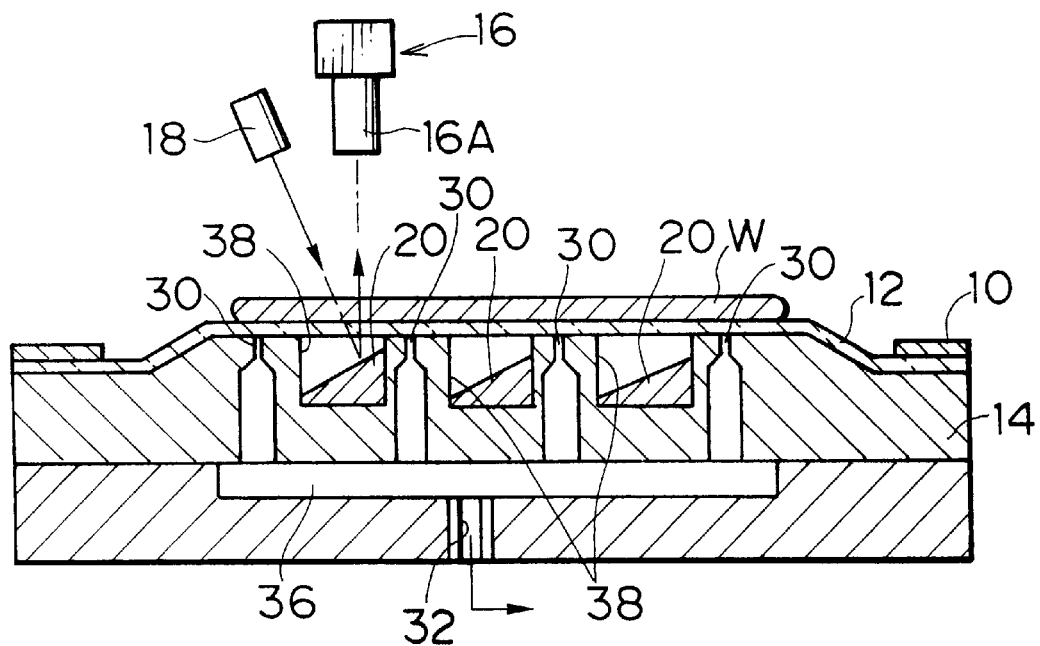
FIG. 3 is a side sectional view showing a wafer table of the wafer pattern imaging apparatus according to the present invention.
Figure 4:
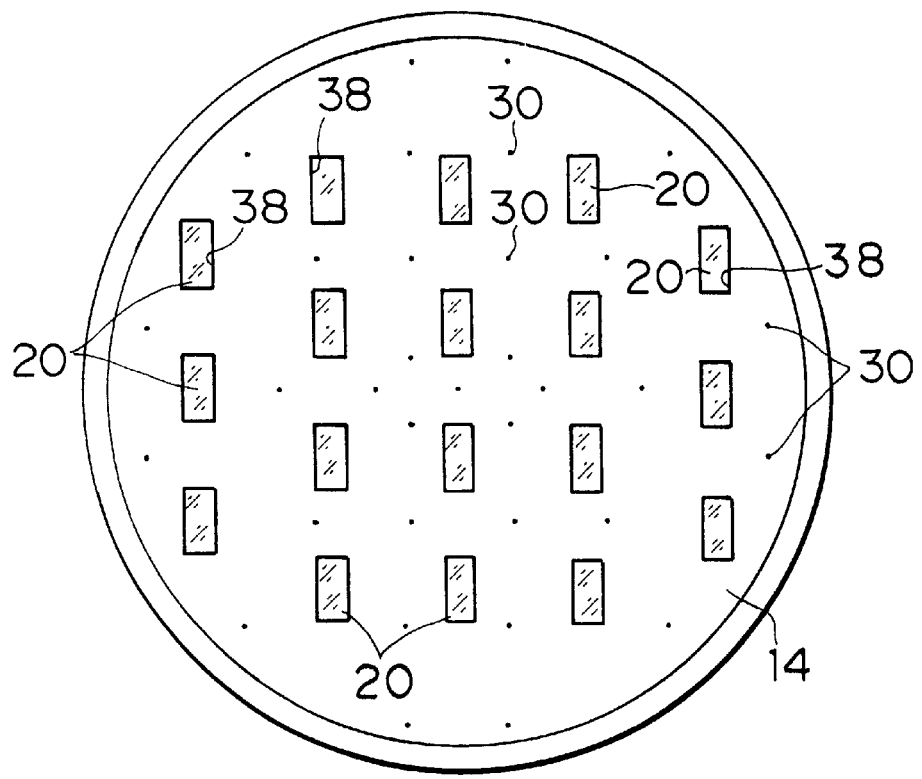
FIG. 4 is a plan view showing the wafer table of the wafer pattern imaging apparatus according to the present invention.

A plurality of mirrors 20 are disposed in the wafer table 14 as indicated by dotted lines in FIG. 2 (see FIGS. 3 and 4, only one mirror 20 is shown in FIG. 2). The mirrors 20 reflect the infrared light.

The infrared light emitted from the IR light source 18 includes light with a wavelength of about 1100 nm that can be transmitted through the wafer W made of silicon. The infrared light diagonally enters the upper surface (the reverse) of the wafer W, and is transmitted through the wafer W and the wafer sheet 12 to enter the mirror 20 disposed in the wafer table 14. Then, the infrared light is reflected vertically on the mirror 20 and illuminates the pattern surface of the wafer W from below.

The IR camera 16 images the pattern surface of the wafer W, which is illuminated with the infrared light. More specifically, the infrared light that is reflected on the mirror 20 is transmitted through the wafer W except parts that are cut off by the patterns on the pattern surface of the wafer W and enters the microscope 16A of the IR camera 16 above the wafer table 14. The microscope 16A enlarges the image in a predetermined range of the pattern surface of the wafer W, and the IR camera 16 images the enlarged image.

FIGS. 3 and 4 are a side sectional view and a plan view, respectively, showing the wafer table 14. The wafer W, which is attached to the wafer sheet 12, is placed with its pattern surface down on the wafer table 14. As shown in FIGS. 3 and 4, a number of suction holes 30 are formed in the top of the wafer table 14, and the suction holes 30 connect to an exhaust hole 32 formed in the bottom of the wafer table 14 through a cavity 36. A suction pump (not shown) connects to the exhaust hole 32. Running the suction pump lowers an air pressure in the cavity 36 of the wafer table 14. This causes the wafer sheet 12 to be held to the top of the wafer table 14 through the vacuum holes 30 by suction. Thus, the wafer W. which is attached to the wafer sheet 12, is fixed on the wafer table 14.

Rectangular holes 38 are formed at a plurality of positions in the top of the wafer table 14. The mirrors 20 for reflecting the infrared light are disposed in the holes 38. The mirrors 20 are distributed in the wafer table 14 so that the IR camera 16 can image the pattern surface of the wafer W over the plurality of positions. The wafer table 14 is moved to move each mirror 20 to the position just below the IR camera 16 in order to image the pattern surface of the wafer W at the position of each mirror 20.

Figure 5:
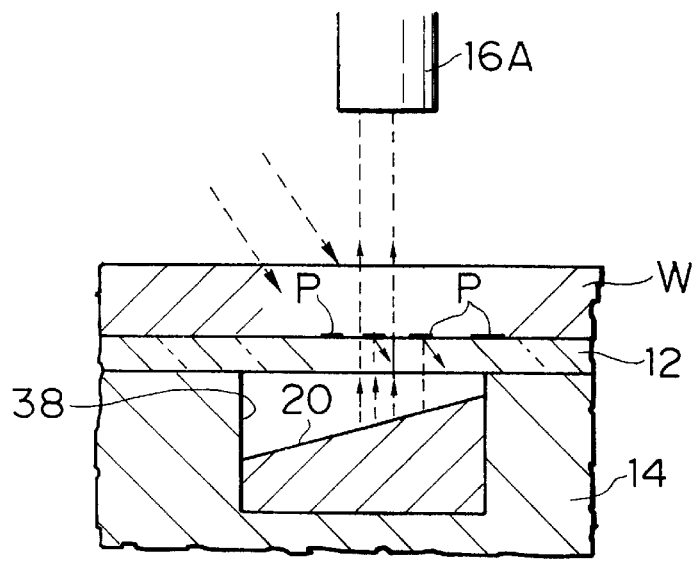
FIG. 5 is an explanation drawing showing infrared light on a pattern surface of a wafer.

As shown in FIG. 3, the reflection planes of the mirrors 20 are inclined at a predetermined angle with respect to the horizontal plane (the top of the wafer table 14). The angle of inclination is determined according to a positional relationship between the IR camera 16 and the IR light source 18. The angle of inclination is determined in such a way that the infrared light that enters the mirror 20 from the IR light source 18 can be reflected onto the optical axis of the IR camera 16 when the normal line of the reflection plane of the mirror 20 and the optical axes of the IR camera 16 and the IR light source 18 are on the same plane. Consequently, as shown in FIG. 5, the infrared light that is reflected onto the optical axis of the IR camera 16 by the mirror 20 is transmitted through the wafer W except for the parts cut off by the patterns P on the pattern surface of the wafer W. Then, the transmitted infrared light enters the microscope 16A of the IR camera 16 disposed above the wafer table 14.

Figure 6:
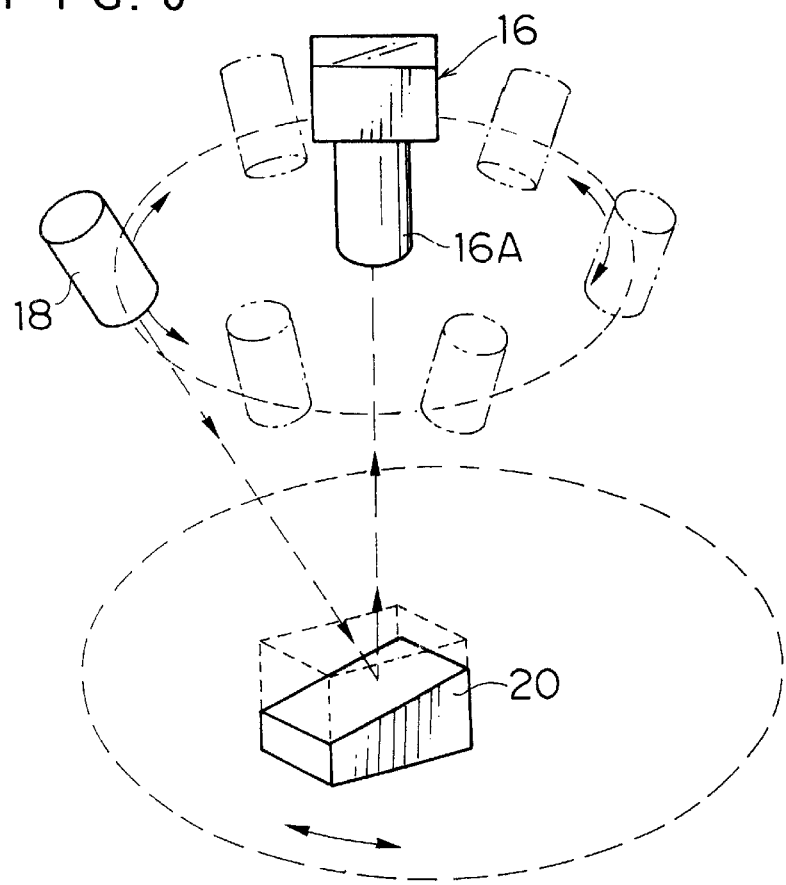
FIG. 6 is an explanation drawing showing the action of an IR light source.
Figure 8:
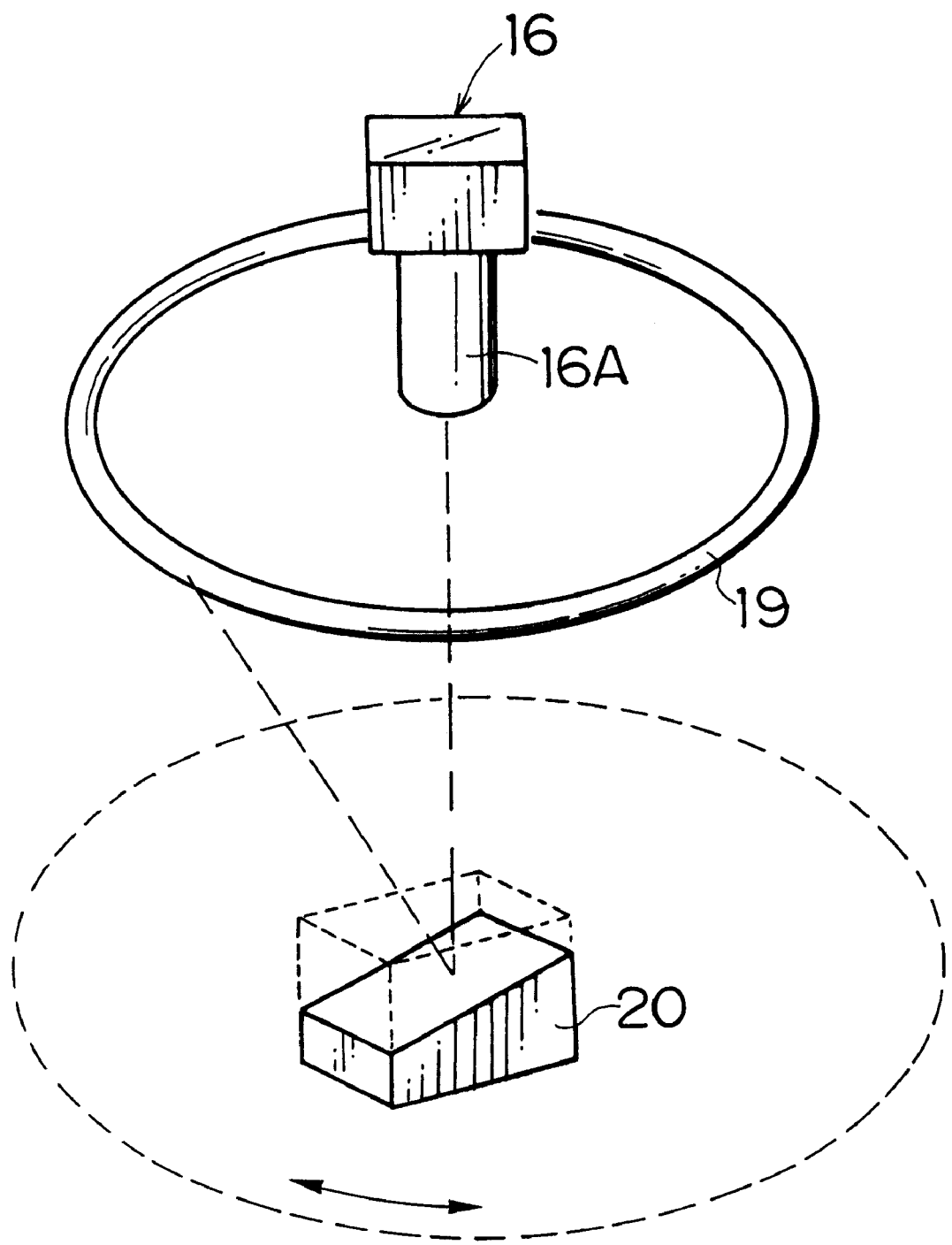
FIG. 8 is a view showing another IR light source.

When the wafer table 14 rotates in the direction θ, there is a change in the incident angle of the infrared light entering the mirror 20. Therefore, the infrared light reflected on the mirror 20 does not enter the IR camera 16. To solve this problem, the IR light source 18 rotates around the IR camera 16 in accordance with the rotational angle of the wafer table 14 as shown in FIG. 6. Thus, the infrared light can always enter the mirror 20 at a constant incident angle, and the infrared light reflected on the mirror 20 properly enters the IR camera 16 just over the mirror 20. Instead of rotating the single IR light source 18, it is also possible to provide a plurality of IR light sources 18 around the IR camera 16 as shown in FIG. 7, and it is also possible to provide a ring-shaped IR light source 19 around the IR camera 16 as shown in FIG. 8, so that the infrared light can always enter the mirror 20 at a constant incident angle when the wafer table 14 rotates.

As stated above, the wafer pattern imaging apparatus illuminates the wafer W with the infrared light, which can be transmitted through the wafer W made of silicon, and images the images formed by the infrared light transmitted through the wafer W, thereby imaging the pattern surface (the obverse) of the wafer W over the reverse of the wafer W. Thus, in the dicing apparatus, it is possible to image the pattern surface at the positions of the mirrors 20 in the wafer table 14, even though the pattern surface of the wafer W is attached to the wafer sheet 12 to protect the pattern surface and the wafer W is placed with its pattern surface down on the wafer table 14. The wafer table 14 is moved or rotated in order to image the pattern surface of the wafer W at the positions of the mirrors 20 and to align the wafer W by matching the images with a stored reference pattern.

In the above-described embodiment, the mirrors 20 are arranged uniformly in the wafer table 14 as shown in FIG. 4. If, however, the pattern surface of the wafer W is imaged only at the front, rear, right and left of the wafer table 14 in the alignment of the wafer W, the mirrors 20 may be arranged according to the imaging positions as shown in FIG. 9.

Figure 10:
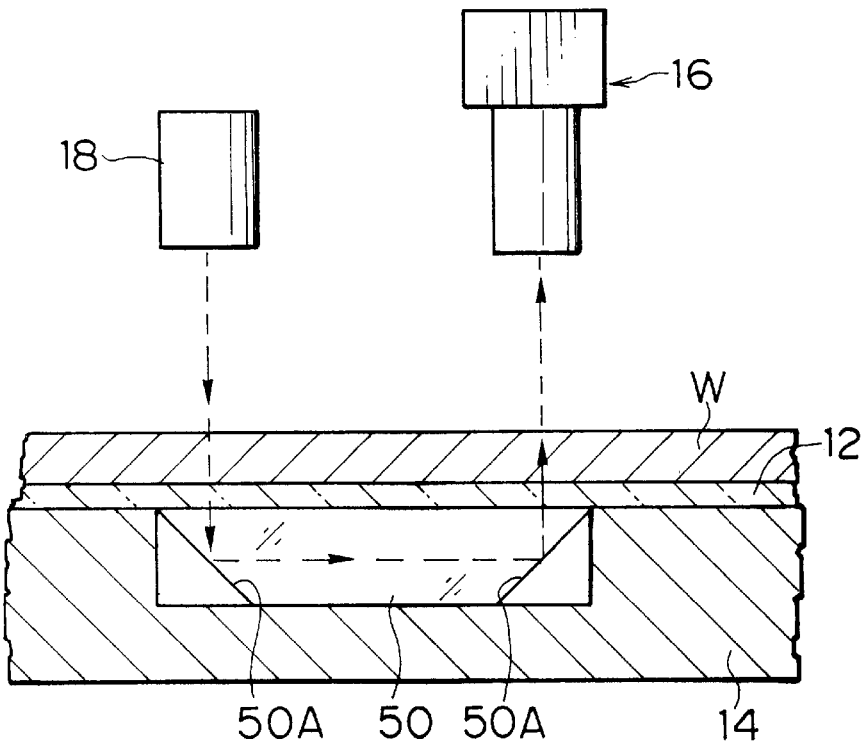
FIG. 10 is a side sectional view showing another preferred embodiment of the mirrors on the wafer table.

In the above-described embodiment, the infrared light is emitted diagonally to the wafer table 14, but the present invention should not be restricted to this. For example, instead of the mirrors 20, optical members 50 such as prisms having two reflection planes 50A, which are inclined at an angle of 45°, are disposed in the wafer table 14 as shown in FIG. 10, and the IR light source 18 emits the infrared light vertically to illuminate the pattern surface of the wafer W through the two reflection planes 50A of the optical members 50.

Figure 11:
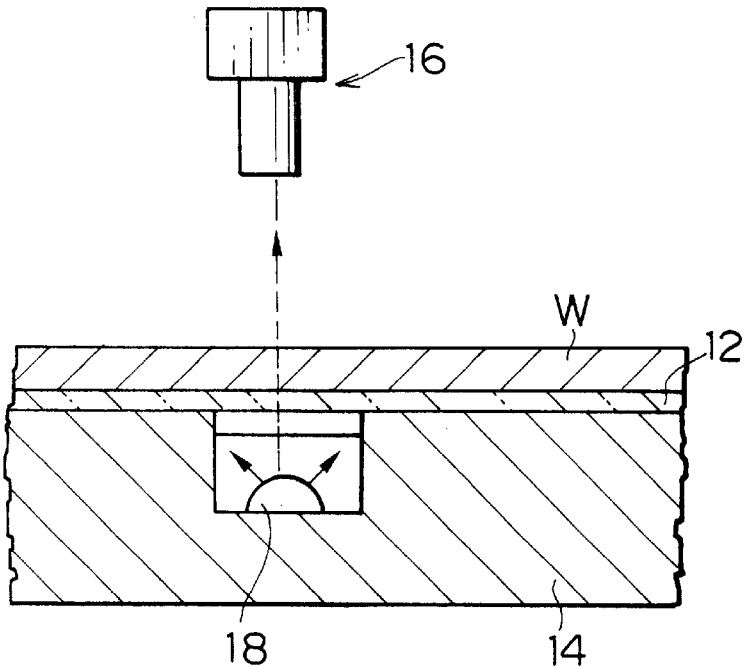
FIG. 11 is a side sectional view showing an embodiment of the wafer table in which the IR light source is disposed.

In the above-described embodiment, the IR light source 18 is disposed above the wafer table 14, and the infrared light is reflected on the mirror 20 disposed in the wafer table 14 to illuminate the pattern surface of the wafer W. The present invention, however, should not be restricted to this. For example, the IR light source 18 may be built in the wafer table 14 as shown in FIG. 11 to illuminate the pattern surface of the wafer W directly or through an optical member such as a mirror. Alternatively, the IR light source 18 may be disposed below the wafer table 14 to illuminate the pattern surface of the wafer W through an optical path such as a hole formed in the wafer table 14. Alternatively, the IR light source 18 and the IR camera 16 may be disposed above the wafer table 14 and in the wafer table 14, respectively.

In the above-described embodiment, the pattern surface is imaged from the reverse of the wafer W by the use of the infrared light transmitted through the wafer W since the pattern surface of the wafer W cannot be imaged by visible light. The present invention, however, should not be restricted to this. For example, even if the wafer W is placed on its pattern surface up on the wafer table 14, the infrared light may be used to image the pattern surface. If the infrared light is used, the obtained images have higher contrast compared with the case where the visible light is used.

In the above-described embodiment, the pattern surface of the wafer W is imaged from the reverse side of the wafer W since the infrared light can be transmitted through the wafer W made of silicon. The material of the wafer W is not restricted to the silicon. It is also possible to image the pattern surface of a wafer, which is made of material other than silicon, from the reverse of the wafer by the use of light that can be transmitted through the wafer. It is also possible to image the pattern surface of the wafer W made of silicon from the reverse of the wafer W by a light, other than the infrared light, that can be transmitted through the wafer W.

The present invention is applied not only to the alignment of the wafer in the wafer dicing apparatus, etc. but also to an apparatus that images the pattern surface of the wafer for some purposes (e.g., a wafer probing machine and a wafer defect detecting machine).

As set forth hereinabove, according to the wafer pattern imaging apparatus of the present invention, the light such as the infrared light, which can be transmitted through the wafer made of silicon, is emitted to illuminate the wafer, and the patterns on the obverse of the wafer is imaged with the light transmitted through the wafer. The patterns on the obverse of the wafer can be imaged from the reverse of the wafer. It is therefore possible to image the patterns on the obverse of the wafer from above the wafer table, even if the obverse of the wafer is attached to the wafer sheet and the wafer is placed with its obverse down on the wafer table in the wafer dicing machine in order to prevent the contaminations from being adhered to the obverse of the wafer, on which the patterns are formed, or prevent the cutting solution from contacting with the obverse of the wafer. The wafer can be aligned in accordance with the obtained images.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A wafer pattern imaging apparatus for imaging patterns on an obverse of a wafer, the wafer pattern imaging apparatus comprising:

an illuminator that emits light to the wafer, the light being transmitted through portions of the wafer where the patterns are not located; and an imaging system that images the patterns on the obverse of the wafer by the light emitted from the illuminator and transmitted through the wafer; wherein:

the wafer is placed with the obverse thereof down on a surface of a wafer table;

the imaging system and the illuminator are disposed above a reverse of the wafer;

a reflection surface that reflects the light emitted from the illuminator and transmitted through the wafer to the imaging system is provided below the surface of the wafer table; and the imaging system images an image formed by the light reflected by the reflection surface.

2. The wafer pattern imaging apparatus as defined in claim 1, wherein the wafer is made of silicon, the light is infrared light, and the imaging system comprises an infrared camera.

3. A wafer pattern imaging apparatus for imaging patterns on an obverse of a wafer, the wafer pattern imaging apparatus comprising:

an illuminator that emits light to the wafer, the light being transmitted through portions of the wafer where the patterns are not located; and an imaging system that images patterns on the obverse of the wafer by the light emitted from the illuminator and transmitted through the wafer; wherein:

the wafer is placed with the obverse thereof down on a surface of a wafer table;

the imaging system is disposed above a reverse of the wafer;

the illuminator is provided below the surface of the wafer table; and the imaging system images an image formed by the light emitted from the illuminator.

4. The wafer pattern imaging apparatus as defined in claim 3, wherein the wafer is made of silicon, the light is infrared light, and the imaging system comprises an infrared camera.

5. A wafer pattern imaging apparatus for imaging patterns on an obverse of a wafer, the wafer pattern imaging apparatus comprising:

an illuminator that emits light to the wafer, the light being transmitted through portions of the wafer where the patterns are not located; and an imaging system that images patterns on the obverse of the wafer by the light emitted from the illuminator and transmitted through the wafer;

wherein the illuminator rotates around an optical axis of the imaging system in association with rotation of the wafer table.

6. The wafer pattern imaging apparatus as defined in claim 5, wherein the wafer is made of silicon, the light is infrared light, and the imaging system comprises an infrared camera.

7. A wafer pattern imaging apparatus for imaging patterns on an obverse of a wafer, the wafer pattern imaging apparatus comprising:

an illuminator that emits light to the wafer, the light being transmitted through portions of the wafer where the patterns are not located; and an imaging system that images patterns on the obverse of the wafer by the light emitted from the illuminator and transmitted through the wafer;

wherein the illuminator comprises a plurality of light sources arranged on a circle around an optical axis of the imaging system.

8. The wafer pattern imaging apparatus as defined in claim 7, wherein the wafer is made of silicon, the light is infrared light and the imaging system comprises an infrared camera.

9. A wafer pattern imaging apparatus for imaging patterns on an obverse of a wafer, the wafer pattern imaging apparatus comprising:

an illuminator that emits light to the wafer, the light being transmitted through portions of the wafer where the patterns are not located; and an imaging system that images patterns on the obverse of the wafer by the light emitted from the illuminator and transmitted through the wafer;

wherein the illuminator comprises a ring-shaped light source arranged on a circle around an optical axis of the imaging system.

10. The wafer pattern imaging apparatus as defined in claim 9, wherein the wafer is made of silicon, the light is infrared light, and the imaging system comprises an infrared camera.

* * * * *